United States Patent [19]

Choksi

[11] 4,360,018

[45] Nov. 23, 1982

[54] ANESTHESIA SYSTEM AND METHOD OF FILTERING RESPIRATORY GAS

[75] Inventor: Pradip V. Choksi, Northridge, Calif.

[73] Assignee: American Hospital Supply Corporation, Evanston, Ill.

[21] Appl. No.: 105,841

[22] Filed: Dec. 20, 1979

[51] Int. Cl.³ .............................................. A61M 16/00
[52] U.S. Cl. ........................ 128/205.12; 128/205.29; 55/DIG. 35; 55/521
[58] Field of Search ............... 128/205.12, 205.28, 128/205.29; 55/521, DIG. 35

[56] References Cited

U.S. PATENT DOCUMENTS

| | | | |
|---|---|---|---|
| 3,556,097 | 1/1971 | Wallace | 128/205.29 |
| 3,713,440 | 1/1973 | Nicholes | 128/205.28 |
| 3,800,510 | 4/1974 | Lamond | 55/521 X |
| 3,815,754 | 6/1974 | Rosenberg | 210/445 |
| 3,867,294 | 2/1975 | Paul et al. | 210/489 |
| 3,932,153 | 1/1976 | Byrns | 55/511 |
| 3,960,148 | 6/1976 | Dryden | 128/205.17 |
| 4,133,656 | 1/1979 | Kippel et al. | 55/274 |
| 4,159,954 | 7/1979 | Gangemi | 210/446 |

FOREIGN PATENT DOCUMENTS

| | | |
|---|---|---|
| 780709 | 4/1952 | United Kingdom . |
| 780710 | 8/1957 | United Kingdom . |
| 892262 | 3/1962 | United Kingdom . |

Primary Examiner—Henry J. Recla
Attorney, Agent, or Firm—Roger A. Williams

[57] ABSTRACT

An anesthesia system with a filter located between a Y-connector and a mask or endotracheal tube for connecting with a patient. The filter operates two ways in that it filters during both inhalation and exhalation of the patient. The filter has a very low pressure drop and is small and compact, with a body having an internal volume of 50 cc or less to prevent the patient from rebreathing large volumes of unfiltered exhaled gas.

4 Claims, 5 Drawing Figures

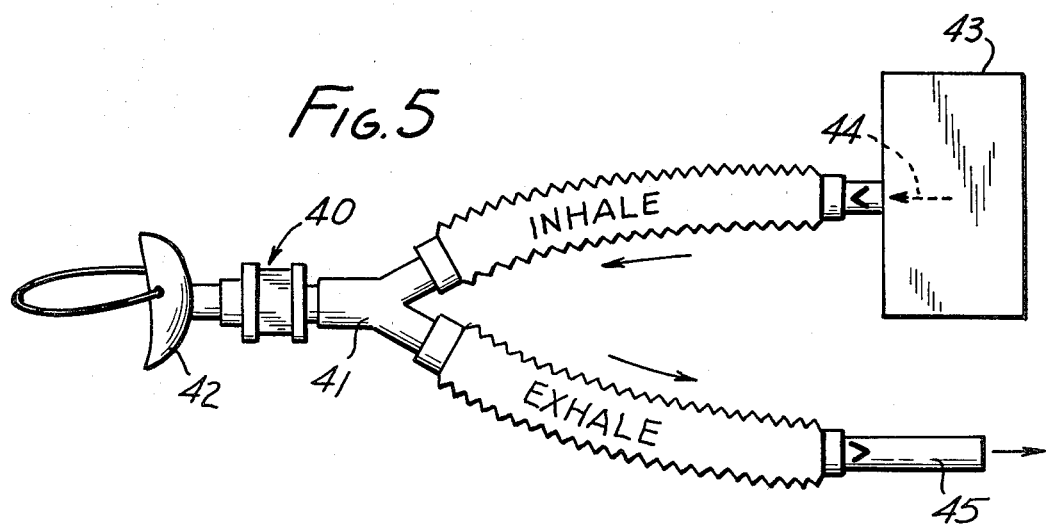

ANESTHESIA SYSTEM AND METHOD OF FILTERING RESPIRATORY GAS

BACKGROUND

The purpose of filters in anesthesia circuits is to protect against cross-contamination between the patient and the anesthesia machine. The same machine is used for many different patients. However, the patient connected elements, such as a mask or endotracheal tube, as well as the Y-connector and corrugated tubing, are usually disposed of after a single patient use to prevent contamination. Because it is of utmost importance to protect the patient from as much of the system as possible, it is desirable to place the filter as close as possible to the patient. In the past, it has not been feasible to place the filter between the Y-connector and the patient because the filter was so bulky as to interfere with the anesthesiologist's view and working area at the patient's oral-nasal area.

It is important to understand that to be effective, an anesthesia gas filter must have a filtering efficiency in excess of 95% and have a very low pressure drop across the filter at relatively high gas flow rates. This is so the filter does not provide a strain to the breathing patient, who often has a weakened respiratory system. For use in an anesthesia circuit, a filter must have a pressure drop of less than 0.3 inch of water at flow rates up to 12.5 L gas/minute. In the past, there have been no anesthesia filters that could meet these requirements and still be compact enough not to interfere with the work of the anesthesiologist adjacent the patient's face. For these reasons, the large anesthesia filters of the past have been located remote from the patient. Usually there were separate filters on the inhalation and exhalation conduits.

U.S. Pat. No. 3,556,097 illustrates a typical recycling anesthesia circuit which is connected to a patient through an oral-nasal mask. This mask is connected through a Y-connector to a corrugated inhalation tube 7 and a corrugated exhalation tube 6. In FIG. 1, filter 9 is typically spaced remote from the patient to filter the incoming respiratory gas.

Although FIG. 14 of U.S. Pat. No. 3,556,097 shows an alternate positioning of the filter between the Y-connector and mask, the filter of this patent could not practically be used in this position because of its immense size, causing the patient to rebreathe a large volume of his unfiltered, exhaled gas. It is estimated the body (excluding connectors) of the filter of U.S. Pat. No. 3,556,097 has an internal volume of 100 cc or more. This very large filter would also likely interfere with the anesthesiologist's view and working area in the patient's oral-nasal area.

The applicant is aware of a filter almost identical to that described in U.S. Pat. No. 3,556,097, being marketed under the Foregger name. Upon applicant's information and belief, this Foregger filter is always placed between the Y-connector and the anesthesia machine. Applicant is unaware of any anesthesiologists using the Foregger filter between the patient and the Y-connector. The filter's immense bulk and problem with rebreathing substantial amounts of unfiltered, exhaled gas is probably the reason for this.

U.S. Pat. No. 3,713,440 illustrates another anesthesia system with filters in the typical position in the corrugated tubing between the Y-connector and the anesthesia machine.

A rectangular filter with pleated filtering elements is described in U.S. Pat. No. 3,815,754. This filter has been sold for use with respiratory therapy equipment in which a respiratory therapy machine drives the respiratory gases across the filter. Thus, the pressure drop across the filter is not as critical as an anesthesia machine where the patient's own breathing provides the driving force for the gas across the filter. The filter of this patent is unsuited for placing in an anesthesia circuit between the Y-connector and the patient because its pressure drop and flow rates up to 12.5 L gas/minute is substantially greater than 0.3 inch of water. Also, its immense physical size (approximately the size of the Foregger filter of the previous paragraph) would interfere with the work of the anesthesiologist in the patient's oral-nasal area.

SUMMARY OF THE INVENTION

The present invention overcomes the above problems by providing an anesthesia system which includes a separate inhalation and exhalation conduit connected to a common duct leading to the patient. In this common duct is a filter to protect against the transfer of contamination between the patient and the remaining portions of the system. This filter meets the requirements for an anesthesia filter adjacent the patient's oral-nasal area, including size, filtering efficiency, and low pressure drop at respiratory flow rates. The respiratory gas is filtered by a method in which the inhalation gas and the exhalation gas are filtered through the same two-way filter. The filter has a housing body (exclusive of adapter) with a very low internal volume of 50 cc or less to prevent the patient from rebreathing any substantial amount of unfiltered, exhaled gas.

RELATED APPLICATIONS

The present application deals with an anesthesia circuit with a filter and method of filtering anesthesia gas. Related co-pending, co-owned applications relating to the structural configuration of the filter housing, how it is assembled, and the particular filter media are as follows:

Housing Construction For Filter, filed Dec. 20, 1979, Ser. No. 105,842, by Choksi, Davidner, and Vidal; Method of Making a Filter, filed Dec. 20, 1979, Ser. No. 105,840, by Choksi, Davidner and Vidal; and Bacterial Filter Media, filed Dec. 20, 1979, Ser. No. 105,819, by Choksi and Davidner.

THE DRAWINGS

FIG. 5 is a schematic view of a second embodiment of the invention showing a nonrecycling anesthesia system with the filter and a patient mask.

DETAILED DESCRIPTION

Figure 1:
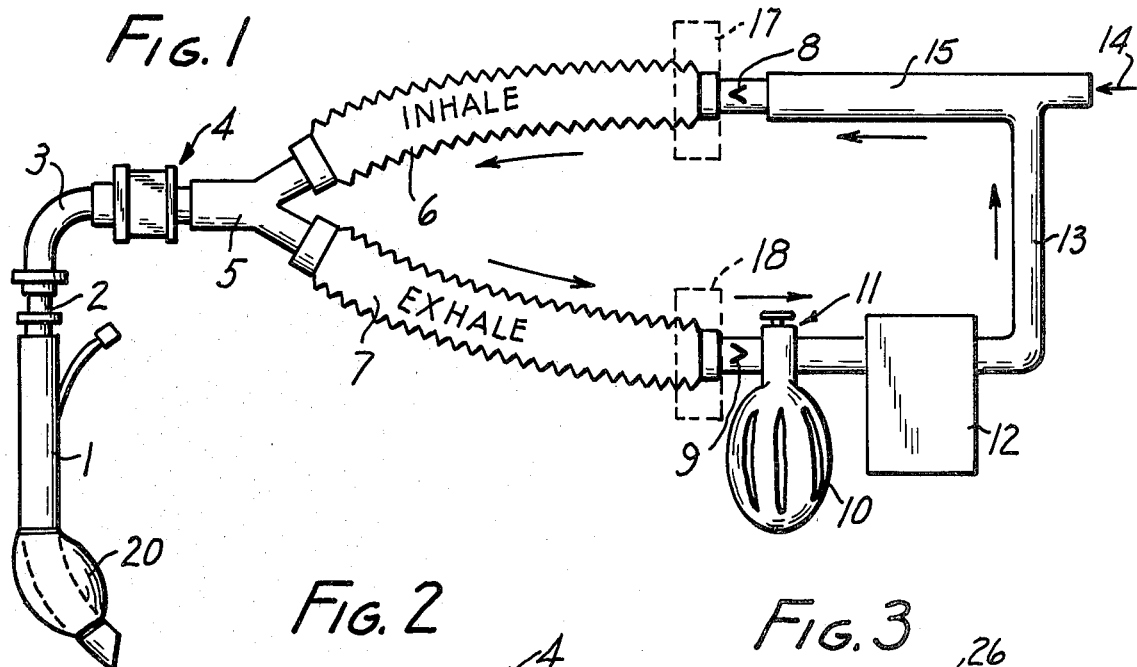
FIG. 1 is a schematic view of a first embodiment of the invention which shows a recycling anesthesia system with the filter and endotracheal tube.
Figure 2:
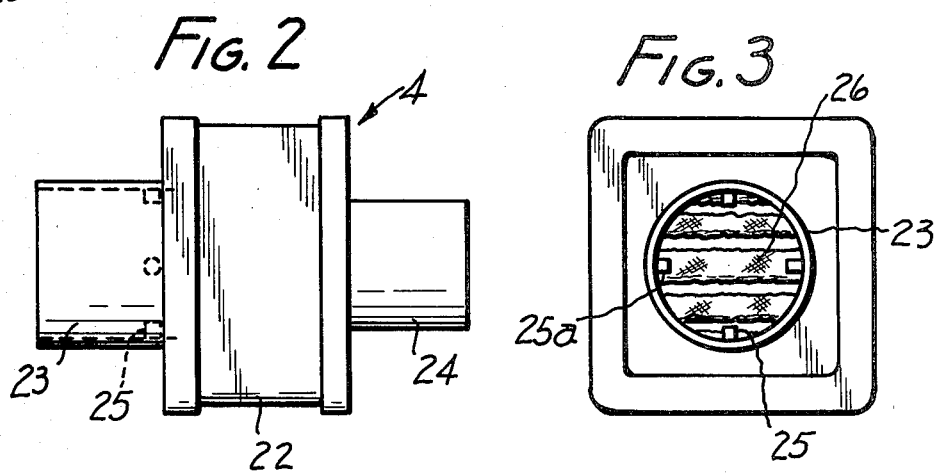
FIG. 2 is an enlarged side elevational view of the filter.

In FIG. 1, an anesthesia circuit is shown connected to a conventional endotracheal tube 1 through an adapter 2 and elbow 3. A filter shown generally at 4 connects to a Y-connector 5 that has arms connecting to separate corrugated inhalation and exhalation tubes shown respectively as 6 and 7. Ends of these corrugated tubes are schematically shown connected to valves 8 and 9. A rebreathing bag 10 controls the breathing pressure in the system and has a pressure relief valve 11. A canister 12, which is well-known in the anesthesia art, removes the carbon dioxide from the exhaled gas. Conduit 13 recycles the carbon dioxide cleansed, exhaled gas and blends it with incoming anesthesia gas 14 entering conduit 15.

The arrows show the direction of respiratory gas flow through the anesthesia recycling system of FIG. 1. This recycling system is the preferred anesthesia system in that a large portion of the expensive anesthesia gas is recycled to the patient. The portion of anesthesia gas consumed by the patient is replenished, as shown by the input at 14.

Except for the filter element 4, the components of the anesthesia system have been used in the past. Frequency separate filters, schematically shown by the dotted lines at 17 and 18, have been located remote from the patient. The patient's location is at the endotracheal tube 1 which is inserted into the patient's throat and trachea. Balloon 20 of the endotracheal tube is inflated against the trachea to form a seal as is well-known with the endotracheal tube art. Thus, the patient's oral-nasal area is very close to the upper end of the endotracheal tube 1.

Figure 3:
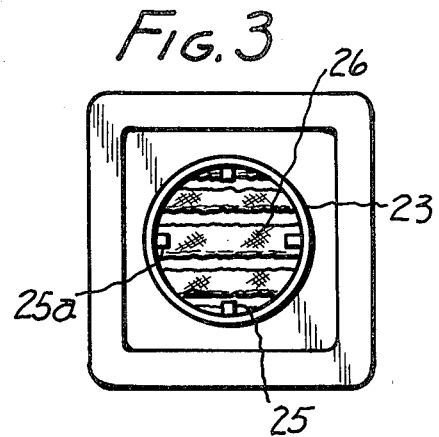
FIG. 3 is a left end elevational view of FIG. 2.

The filter 4 includes a body 22 with tubular connectors 23 and 24. In the left end view of the fiter as shown in FIG. 3, the connector 23 has a series of internal lugs 24 and 25 which are spaced from an outer end of connector 23. This construction in the connector prevents elbow 3 from extending too far into connector 23 and rupturing the cleaned filter element 26.

Figure 4:
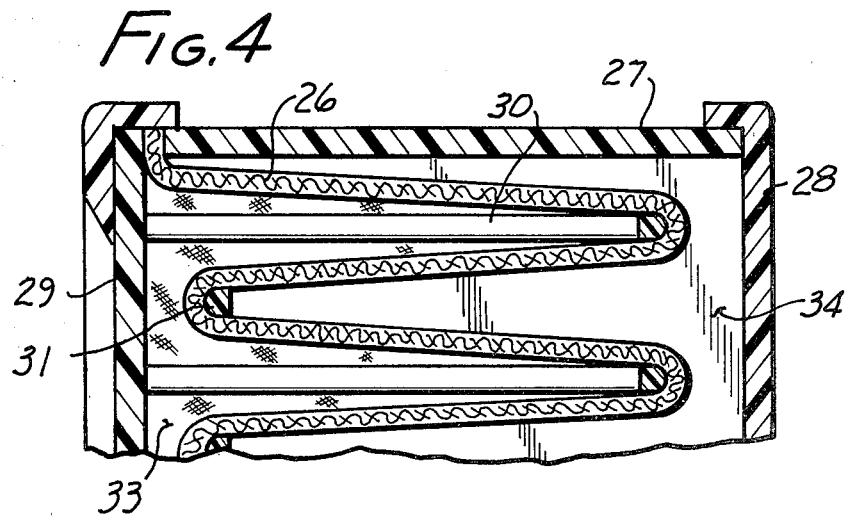
FIG. 4 is a further enlarged fragmentary sectional view of the interior of the filter.

In FIG. 4, the filter housing body includes a rectangular wall 27 with end members 28 and 29 sealed to side wall 27. The pleated filtering element 26 is held in its pleated condition by structural supports shown generally at 30 and 31. The specific construction of the filter housing and the filter media itself is explained in more detail in the related patent applications referenced above.

Because of the particular location of the filter 4, it is important that the internal volume of the filter body, excluding the connectors, be kept to a minimum to reduce the amount of exhaled air that is rebreathed by the patient. The space within the body designated at numeral 34 is on the patient's side, while the space within the filter body designated at numeral 33 is on the machine side of the filter. It has been found that the rectangular housing of FIG. 3 can have a dimension on each side approximately 2 inches and the pleated construction of the specific filter element 26 can be contained in a housing with an internal volume of 50 cc or less (exclusive of adapters). The housing's external volume is 75 cc or less, also exclusive of adapters. Such filter can filter respiratory gas, including an anesthesia gas, at an efficiency greater than 95%. Preferably, the filter efficiency is approximately 99%.

Filters of this efficiency have been made in the past for various uses. However, because of the dense compaction of the filtering media, it took a large pressure differential across the filtering media to drive the gas across the filter element. These are unsuited for anesthesia filters which have a driving force of the gas generated by the patient's breathing. The present very compact filter, which has no lateral dimension greater than 3 inches, and an internal volume of 50 cc or less can filter at an efficiency greater than 95% and still maintain a low pressure drop of less than 0.3 inch at gas flow rates up to 12.5 L gas/minute. Thus, the patient is getting very efficient filtration without straining his breathing. The filter is also very lightweight so it is easily supported on a mask or endotracheal tube.

Within the filter housing is a filter element of naturally hydrophobic thermoplastic material that requires no additional coating. Preferably, the filter element is a nonwoven polypropylene material.

FIG. 5 shows a second embodiment of the invention in which a filter, shown generally at 40, is connected between a Y-connector 41 and an anesthesia mask 42 adapted to fit to the patient. Mask 42 in an alternate ducting means to the endotracheal tube for connecting the anesthesia gas to the patient. Mask 42 would fit over the nose and mouth of the patient.

FIG. 5 also has a different anesthesia circuit in that all of the anesthesia joined to the patient comes from an anesthesia source, shown schematically at 43, and enters the system as shown by the arrow 44. After a portion of the anesthesia has been absorbed by the patient's lungs, the excess anesthesia gas is vented and discarded through conduit 45 as schematically shown. Thus, in FIG. 5 the anesthesia circuit is not recycling and a certain amount of anesthesia gas is lost. While some noncirculating anesthesia circuits are still in use, the preferred circuit is shown in FIG. 1 which recycles the anesthesia gas.

In the foregoing description, specific examples have been used to describe the invention. However, it is understood by those skilled in the art that modifications can be made to the above example without departing from the spirit and scope of the invention.

I claim:

1. A anesthesia system having an inhalation conduit and an exhalation conduit joined via a Y-connector to a common duct that includes means for connecting with a patient, wherein the improvement comprises: an anesthesia gas filter in the common duct having a filtration efficiency in excess of 95%, said filter comprising a housing body having an internal volume of 50 cc or less; a pleated hydrophobic filter element sealed in said housing body having a pressure drop of less than 0.3 inch of water at gas flow rates up to 12.5 L gas/minute; and connectors, for attaching said filter between the Y-connector and the common duct, attached at opposite ends of said housing body to form a passage through which respiratory gas can be driven through said filter by normal breathing of the patient.

2. An anesthesia system as defined in claim 1 wherein said means for connecting with a patient comprises an endotracheal tube.

3. An anesthesia system as defined in claim 1 wherein said means for connecting with a patient comprises an anesthesia mask.

4. A method of filtering anesthesia respiratory gas comprising the steps of:
 (a) transferring incoming anesthesia respiratory gas through a first conduit to a two-way filter having a filtration efficiency in excess of 95%, which filter comprises a housing body and having an internal volume of 50 cc or less, a pleated hydrophobic filter element sealed in said housing body having a pressure drop of less than 0.3 inch of water at gas flow rates up to 12.5 L gas/minute;

(b) filtering the incoming gas through such two-way filter;
(c) infusing the filtered incoming gas into the respiratory tract of a patient;
(d) expelling the gas from the respiratory tract of such patient;
(e) filtering the expelled gas through the same two-way filter;
(f) transferring the expelled gas through a second conduit; and
(g) transferring additional incoming respiratory gas through the first conduit to the two-way filter and then into the respiratory tract of a patient, whereby such patient cannot rebreathe a large volume of his unfiltered previously exhaled gas.

* * * * *